United States Patent [19]
Vardimon

[11] Patent Number: 5,906,976
[45] Date of Patent: May 25, 1999

[54] METHOD AND COMPOSITION FOR TREATING NEURONAL DEGENERATION

[75] Inventor: Lily Vardimon, Tel Aviv, Israel

[73] Assignee: Ramot-University Authority for Applied Research and Industrial Development, Ltd., Tel Aviv, Israel

[21] Appl. No.: 08/735,018

[22] Filed: Oct. 22, 1996

[51] Int. Cl.⁶ .................................................. A61K 38/43
[52] U.S. Cl. .............................. 514/12; 514/2; 514/26; 424/94.1
[58] Field of Search ................................ 514/2, 12, 26, 514/179; 424/94.1

[56] References Cited

U.S. PATENT DOCUMENTS

| | | | |
|---|---|---|---|
| 4,439,196 | 3/1984 | Higuchi | 604/890 |
| 4,447,224 | 5/1984 | DeCant, Jr. et al. | 604/67 |
| 4,447,233 | 5/1984 | Mayfield | 604/152 |
| 4,475,196 | 10/1984 | La Zor | 371/29 |
| 4,486,194 | 12/1984 | Ferrara | 604/897 |
| 4,487,603 | 12/1984 | Harris | 604/152 |
| 4,554,271 | 11/1985 | Braughler et al. | 514/179 |
| 4,866,042 | 9/1989 | Neuwelt | 514/44 |
| 4,959,217 | 9/1990 | Sanders et al. | 424/473 |
| 5,013,558 | 5/1991 | Konishi | 424/520 |
| 5,135,956 | 8/1992 | Borg et al. | 514/724 |
| 5,162,375 | 11/1992 | Nichlson et al. | 514/646 |
| 5,167,616 | 12/1992 | Haak et al. | 604/20 |
| 5,169,383 | 12/1992 | Gyory et al. | 604/20 |
| 5,225,182 | 7/1993 | Sharma | 424/9 |
| 5,395,822 | 3/1995 | Izumi et al. | 514/3 |
| 5,428,069 | 6/1995 | Skolnick et al. | 514/531 |
| 5,444,095 | 8/1995 | Tatton et al. | 514/654 |
| 5,455,044 | 10/1995 | Kim et al. | 424/450 |
| 5,464,764 | 11/1995 | Capecchi et al. | 435/172.3 |
| 5,487,992 | 1/1996 | Capecchi et al. | 435/172.3 |
| 5,558,852 | 9/1996 | Bigner et al. | 424/1.49 |

OTHER PUBLICATIONS

Gorovits, et al. "Glutamine synthetase protects against neuronal degeneration in injured retinal tissue" *Proc. Natl. Acad. Sci. USA*, vol. 94, pp. 7024–7029 (1997).

Jackowski, Andre, "Neural injury repair: hope for the future as barriers to effective CNS regeneration become clearer" *British Journal of Neurosurgery*, 9, 303–317 (1995).

Stull, et al. "Antigene, Ribozyme and Aptamer Nucleic Acid Drugs: Progress and Prospects" *Pharmaceutical Research*, vol. 12, No. 4 (1995).

Ankarcrona et al., "Glutamate–induced neuronal death: a succession of necrosis or apoptosis depending on mitochondrial function" *Neuron*, 15:961–973 (1995).

Ben Dror et al., "Developmental control of glucocorticoid receptor transcriptional activity in embryonic retina" *Proc. Natl. Acad. Sci. USA*, 90:1117–1121 (1993).

Betz et al., in *Basis Neurochem. Molecular Cell*, Raven Press Ltd., NY 5th edition, pp. 681–699 (1994).

Berko Flint et al., "Involvement of c–Jun in the control of glucocorticoid receptor transcriptional activity . . ." *EMBO J.*, 13:646–654 (1994).

Bickel et al., "Pharmacologic effects in vivo in brain by vector–mediated peptide drug delivery" *Proc. Natl. Acad. Sci. USA*. 90(7):2618–2622 (1993).

Bonfoco et al., "Apoptosis and necrosis: two distinct events induced, respectively, by mild and intense insults . . ." *Proc. Natl. Acad. Sci. USA*, 92:7162–7166 (1995).

Bracken et al., "A randomized, controlled trial of methylprednisolone or naloxone in the treatment of acute spinal–cord injury . . ." *N. Engl. J. Med.*, 322:1405–1411 (1990).

Braughler et al., "Evaluation of an intensive methylprednisilone sodium succinate dosing regimen in experimental spinal cord injury" *J. Neurosurg.*, 67:102–105 (1987).

Brem et al., "Polymers as controlled drug delivery devised for the treatment of malignant brain tumors" *Eur. J. Pharm. Biopharm*, 39:2–7 (1993).

Brune et al., "Spermine prevents endonuclease activation and apoptosis in thymocytes" *Exp. Cell Res.*, 195:323–329 (1991).

Calne et al., "Alzheimer's disease, Parkinson's disease, and motoneurone disease: abiotrophic interaction . . ." *Lancet*, 2:1067–1070 (1986).

Choi, "Glutamate neurotoxicity and diseases of the nervous system" *Neuron*, 1:623–634 (1988).

Choi, "Calcium: still center–stage in hypoxic–ischemic neuronal death" *Trends Neurosci.*, 18:58–60 (1995).

Choi and Rothman, "The role of glutamate neurotoxicity in hypoxic–ischemic neuronal death" *Annu. Rev. Neurosci.*, 13:171–182 (1990).

Clifford et al., "Ketamine and MK–801 prevent degeneration of thalamic neurons injured by focal cortical seizures" *Exp. Neurol.*, 105:272–279 (1989).

Coyle and Schwarz, "Lesion of striatal neurons with kainic acid provides a model for Huntington's chorea" *Nature*, 263:244–246 (1976).

David et al., "Involvement of excitatory neurotransmitters in the damage produced in chick embryo retinas . . ." *Exp. Eye Res.*, 46:657–662 (1988).

Drejer et al., "Cellular origin of ischemia–induced glutamate release from brain tissue in vivo and in vitro" *J. Neurochem.*, 45:145–151 (1985).

Dubinsky and Rothman, "Intracellular calcium concentrations during "chemical hypoxia" and excitotoxic neuronal injury" *J. Neurosci.*, 11:2545–2551 (1991).

(List continued on next page.)

*Primary Examiner*—Paula K. Hutzell
*Assistant Examiner*—Robert C. Hayes
*Attorney, Agent, or Firm*—Kohn & Associates

[57] ABSTRACT

A pharmaceutical composition and method for treating injury to or diseases which result in neuronal degeneration resulting from stroke, brain, retina or spinal cord injuries and other brain disorders and possible trauma associated with neurosurgical procedures is disclosed. The composition consists of glutamine synthetase (GS), analogues and derivatives thereof and a pharmaceutical carrier which when administered to a patient prevents or reduces neuronal degeneration.

7 Claims, 8 Drawing Sheets

OTHER PUBLICATIONS

Dykens et al., "Mechanism of kainate toxicity to cerebellar neurons in vitro is analagous to reperfusion tissue injury" *J. Neurochem.*, 49:1222–1228 (1987).

Gibbs et al., "Sequence of a human glutamine synthetase cDNA" *Nucleic Acid Res.*, 15:6293 (1987).

Gilboa et al., "Transfer and expression of cloned genes using retroviral vectors" *BioTechniques*, 4(6):504–512 (1986).

Gorovits et al., "Developmental changes in the expression and compartmentalization of theglucocorticoid receptor . . . " *Proc. Natl. Acad. Sci. USA*, 91:4786–4790 (1994).

Grossman et al., "Molecular basis for differential expression of glutamine synthetase in retina glia and neurons" *Brain Res. Mol. Brain Res.*, 21:312–320 (1994).

Gunnersen and Haley, "Detection of glutamine synthetase in the cerebrospinal fluid of Alzhemier diseased patients . . . " *Proc. Natl. Acad. Sci. USA*, 89:11949–11953 (1992).

Hall, "High–dose glucocorticoid treatment improves neurological recovery in head–injured mice" *J. Neurosurg.*, 62:882–887 (1985).

Heron et al., "Regional variability in DNA fragmentation after global ischemia evidenced by combined histological and gel . . . " *J. Neurochem.*, 61:1973–1976 (1993).

Koh and Choi, "Quantitative determination of glutamate mediated cortical neuronal injury in cell culture by lactate . . . " *J. Neurosci. Methods.*, 20:83–90 (1987).

Kramer et al., "Gene transfer through the blood–nerve barrier: NGF–engineered neuritogenic T lymphocytes . . . " *Nature Medicine*, 1:1162–1166 (1995).

Kure et al., "Glutamate triggers internucleosomal DNA cleavage in neuronal cells" *Biochem. Biophys. Res. Commun.*, 179, 39–45 (1991).

Linnik et al., "Evidence supporting a role for programmed cell death in focal cerbral ischemia in rats" *Stroke*, 24:2002–2009 (1993).

Linser and Moscona, "Induction of glutamine synthetase in embryonic neural retina: localization in Muller fibers and dependence . . . " *Proc. Natl. Acad. Sci. USA*, 76:6476–6480 (1979).

Linser and Moscona, "Hormonal induction of glutamine synthetase in cultures of embryonic retina cells: requirement for neuron–glia . . . " *Dev. Biol.*, 96:529–534 (1983).

Louzada, Jr. et al., "Glutamate release in experimental ischaemia of the retina: an approach using microdialysis" *J. Neurochem.*, 59:358–363 (1992).

Macmanus et al., "Global ischemia can caused DNA fragmentation indicative of apoptosis in rat brain" *Neurosci. Lett.*, 164:89–62 (1993).

Maragos et al., "Glutamate dysfunction in Alzehimer's disease: an hypothesis" *TINS*, 10:65–68 (1987).

Mattson, "Excitory amino acids, growth factors and calcium: a teeter–totter model for neural plasticity and degeneration" *Adv. Exp. Med. Biol.*, 268:211–220 (1990a).

Mattson, "Antigenic changes similar to those seen neurofibrillary tangles are elicited by glutamate and Ca2+ influx . . . " *Neuron*, 4:105–117 (1990b).

Meister, in *Biochemical Modulation of Anticancer: Experimental and Clinical Approaches*, eds. Valeriote, F.A. and Baker, L.H. Martinus Nijhoff Pub., Boston . . . , pp. 245–259 (1989).

Michaels and Rothman, "Glutamate neurotoxicity in vitro: antagonist pharmacology and intracellular calcium concentrations" *J. Neurosci.*, 10:283–292 (1990).

Moscona, in *Progress in Retinal Research*, eds. Osborne, N.N. and Chader, G.J., Permagon Press, Oxford, 2:111–135 (1983).

Moscona et al., "Enzyme induction in embryonic retina: the role of transcription and translation" *PNAS (USA)*, 61:160–167 (1968).

Mosinger et al., "Blockade of both NMDA and non–NMDA receptors is required for optimal protection against ischmeic neuronal . . . " *Exp. Neurol.*, 113:10–17 (1991).

Moudy et al., "Rapid desensitization determines the pharmacology of glutamate neurotoxicity" *Neuropharmacology*, 33:953–962 (1994).

Nadler et al., "Intraventricular kainic acid preferentially destroys hippocampal pyramidal cells" *Nature*, 271:676–677 (1978).

Neal et al., "Effects of ischaemia on neurotransmitter release from the isolated retina" *J. Neurochem.*, 62:1025–1033 (1994).

Neuwelt et al., "Is there a therapeutic role for blood–brain barrier disruption?" *Ann. Int. Med.*, 93:137–139 (1980).

Norenberg, "Immunohistochemical study of glutamine synthetase in brain trauma" *J. Neuropathol. Exp. Neurol.*, 4:347 (1982).

Olney et al., "The role of specifications in glutamate neurotoxicity" *Neurosci. Lett.*, 65:65–71 (1986).

Olney et al., "NMDA antagonist neurotoxicity: mechanism and prevention" *Science*, 254:1515–1518 (1991).

Olney, "Glutamate, a neurotoxic transmitter" *J. Child Neurol.*, 4:218–226 (1989).

Olney, "New mechanisms of excitatory transmitter neurotoxicity" *J. Neural. Transm. Suppl.*, 43:47–51 (1994a).

Olney, "Neurotoxicity of NMDA receptor antagonists: an overview" *Psychopharmacol. Bull.*, 30:533–540 (1994b).

Pardridge et al., "Blood–brain barrier and new approaches to brain drug delivery" *West J. Med.*, 156(3):281–286 (1992).

Pardridge, "Recent developments in peptide drug delivery to the brain," *Pharm. Toxicol.*, 71(1):3–10 (1992).

Patejunas and Young, "Developmentally regulated primary glucocorticoid hormone induction of chick retinal glutamine . . . " *J. Cell. Biochem.*, 35:205–216 (1987).

Petito et al., "Brain glutamine synthetase increases following cerebral ischemia in the rat" *Brain Res.*, 569:275–280 (1992).

Reisfeld and Vardimon, "Cell to cell contacts control the transcription activity of the glucocorticoid receptor" *Mol. Endocrinol.*, 8:1224–1233 (1994).

Ronzio et al., "Studies on the mechanism of inhibition of glutamine synthetase by methionine sulfoximine" *Biochemistry*, 8:1066–1075 (1969).

Rosner et al., "Methylprednisoline ameliorates retinal photic injury in rats" *Arch. Opthalmol.*, 110:857–861 (1992a).

Rosner et al., "Therapeutic parameters of methylprednisoline treatment for retinal photic injury in a rat model" *Res. Commun. Chem. Pathol. Pharmacol.*, 77:299–311 (1992b).

Rothman, "Synaptic release of excitatory amino acid neurotransmitter mediates anoxic neuronal death" *J. Neurosci.*, 4:1884–1891 (1984).

Rowe et al., "Glutamine synthestase (sheep brain)" in *Methods in Enzymology*, (eds. Tabor, H. and Tabor, C.W.) Academic Press, New York, 17A:900–910 (1970).

Sandberg et al., "Effect of cortico–striate pathway lesion on the activities of enzymes involved in synthesis . . . "*J. Neurochem.*, 44:42–47 (1985).

Simon et al., "Blockade of N–methyl–D–aspartate receptors may protect against ischemic damage in the brain" *Science*, 226:850–852 (1984).

Spencer et al., "Lathyrism: evidence for role of the neuroexcitory amino acid BOAA" *Lancet*, 239:1066–1067 (1986).

Tanaka et al., "Reaction of astrocytes in the gerbil hippocampus following transient ischemia: immunohistochemical . . . " *Exp. Neurol.*, 116:264–274 (1992).

Tecoma et al., "Traumatic neuronal injury in vitro is attenuated by NMDA antagonists" *Neuron*, 2:1541–1545 (1989).

Var den Berg and Garfinkel, "A simulation study of brain compartments–Metabolism of glutamate and related substances in mouse brain" *Biochem. J.*, 123:211–218 (1971).

Vardimon et al., "Development regulation of glutamine synthestase and carbonia anhydrase II in neural retina" *Proc. Natl. Acad. Sci., USA*, 83:9060–9064 (1986).

Vardimon et al., "Cell contacts are required for induction by cortisol of glutamine synthetase gene transcription in the retina" *Proc. Natl. Acad. Sci., USA*, 95:5981–5985 (1988).

Waniewski and Martin, "Exogneous glutamate is metabolized to glutamine and exported by rat primary astrocyte cultures" *J. Neurochem.*, 47:304–313 (1986).

Waniewski and Martin, "Characterization of L–glutamic acid transport by glioma cells in culture . . " *J. Neurochem.*, 4:2237–2246 (1984).

Wilkens and Rengachary, in *Neurosurgery*, vol. II, Chapter 190 (McGraw Hill) "Pathology of closed head injury", pp. 1544–1570 (1982).

Zeevalk et al., "Excitatory amino acid–induced toxicity in chick retina: amino acid release, histology . . . " *J. Neurochem.*, 53:1610–1619 (1989).

Zeevalk and Nicklas, "Chemically induced hypoglycemia and anoxia: relationship to glutamate receptor–mediated . . . " *J. Pharmacol. Exp. Ther.*, 253:1285–1292 (1990).

Herrera et al. Neuroscience 35 (1990) 273–281.

Rudinger In "Peptide Hormones" (Jun. 1976) ed. J.A. Parsions, University Park Press, Baltimore, pp. 1–7.

Sigma Catalog, 1990, p. 523.

METHOD AND COMPOSITION FOR TREATING NEURONAL DEGENERATION

BACKGROUND OF THE INVENTION

1. Technical Field

The present invention relates to compositions for and a method of treatment of neuronal degeneration due to stroke, brain, retina or spinal cord injuries and other brain or retinal disorders by glucocorticoids or glutamine synthetase.

2. Background Art

Neuronal degeneration as a result of stroke, brain, retina or spinal cord injuries, ischemia and reperfusion and other brain or retinal disorders is an enormous medical and public health problem by virtue of both its high incidence and the frequency of long-term sequelae. The pathophysiology of neuronal degeneration has been shown to be directly related to the neurotransmitter glutamate. Upon injury or upon ischemic insult, the damaged neurons release massive amounts of the neurotransmitter glutamate, which is excitotoxic to the surrounding neurons [Choi, 1988; Rothman and Olney, 1986; Choi and Rothman, 1990; David et al., 1988; Drejer et al., 1985]. See also U.S. Pat. No. 5,135,956 issued Aug. 4, 1992 particularly columns 1–8 and U.S. Pat. No. 5,395,822 issued Mar. 7, 1995 columns 1–3 for a review, incorporated herein in their entirety by reference.

Under normal conditions, accumulation of glutamate in the extracellular space is prevented by the operation of a recycling mechanism which serves to maintain neuronal glutamate levels despite continual loss through transmitter release [Van der Berg and Garfinkel, 1971; Kennedy et al., 1974]. Glutamate, released by glutaminergic neurons, is taken up into glial cells where it is converted into glutamine by the enzyme glutamine synthetase [L-glutamate: ammonia ligase (ADP-forming; EC 6.3.1.2)] (GS); glutamine reenters the neurons and is hydrolyzed by glutaminase to form glutamate, thus replenishing the neurotransmitter pool. This biochemical pathway may also serve as an endogenous neuroprotective mechanism, which functions by removing the synaptically released glutamate from the extracellular space and converting it to the nontoxic amino acid glutamine before toxicity occurs. This neuroprotective mechanism fails, however, to prevent glutamate neurotoxicity after insult.

Massive release of glutamate to the extracellular fluid stimulates a cascade of events that amplifies the initial trauma and causes the damage to spread to the neighboring cells [Mattson, 1990a; Olney, 1989; Olney, 1994a]. This biochemical cascade of induction and progression may continue for hours or days and causes delayed neuronal death. The object of medical therapy is to break or eliminate this cascade process and thus prevent spread of the secondary damage.

Involvement of glutamate in neuronal degeneration is supported by three major lines of evidence.

I. Neuronal insult leads to accumulation of relatively high levels of glutamate in the extracellular fluid [Drejer et al., 1985; Waniewski and Martin, 1986].

II. Administration of glutamate (systematically or in vitro) leads to neuronal cell death [Mattson, 1990b; Michaels and Rothman, 1990].

III. Glutamate receptor antagonists can protect from neuronal degeneration [Clifford et al., 1998; Mosinger et al., 1991; Olney, 1994b; Olney et al., 1991].

The mechanism responsible for the glutamate mediated cellular damage and death is not fully understood. However, accumulating evidence supports the hypothesis that glutamate neurotoxicity is mediated through NMDA and non-NMDA-type glutamate excitatory receptors [Simon et al., 1984; Tecoma et al., 1989; Mosinger et al., 1991; Olney et al., 1991] and entails sustained depolarization of postsynaptic dendrosomal membranes, increased membrane permeability and impaired ion homeostasis [Olney, 1989; Moudy et al., 1994; Waniewski and Martin, 1984; Olney et al., 1986; Dubinsky and Rothman, 1991; Choi, 1995] and lead to either an apoptotic or a necrotic type of death [Bonfoco et al., 1995; Ankarcrona et al., 1995]. Although definitive evidence implicating specific ions has been lacking, several studies proposed that excessive calcium influx into the postsynaptic neuron may be responsible for activating signaling pathways and possibly endonucleases which cause neuronal cell death [Olney, 1994; Michaels and Rothman, 1990; Dubinsky and Rothman, 1991].

Several studies have shown the involvement of glutamate in the pathophysiology of Huntington's disease (HD) [Coyle and Schwarcz, 1976], Alzheimer's disease (AD)[Maragos et al, 1987], epilepsy [Nadler et al, 1978], lathyrism [Spencer et al, 1986], amyotrophic lateral sclerosis (ALS) and Parkinsonian dementia of Guam [Calne et al, 1986] as well as in the neuropathology associated with stroke, ischemia and reperfusion [Rothman, 1984; Dykens et al, 1987].

U.S. Pat. No. 5,135,956 discloses treating neuronal degeneration by treating with a long-chain fatty alcohol which has cytoprotective effect. U.S. Pat. No. 5,395,822 discloses treating neuronal degeneration with a salt of pyruvic acid. Further U.S. Pat. Nos. 5,444,095, 5,428,069, 5,162,375 and 5,013,558 disclose other compounds for the treatment of neuronal degeneration. However, none of these approaches utilizes glutamine synthetase to block the cascade resulting in neurotoxicity at the initiation step by directly neutralizing the activity of its trigger: glutamate.

SUMMARY OF THE INVENTION

According to the present invention, a pharmaceutical composition and method for treating injury to or diseases which result in neuronal degeneration resulting from stroke, brain, retina or spinal cord injuries and other brain or retinal disorders and possible trauma associated with neurosurgical procedures or laser treatments is disclosed. The composition consists of glutamine synthetase (GS), analogues and derivatives thereof and a pharmaceutical carrier which when administered to a patient prevents or reduces neuronal degeneration. Alternatively, gene therapy utilizing the gene for glutamine synthetase can be employed.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

Figure 1:
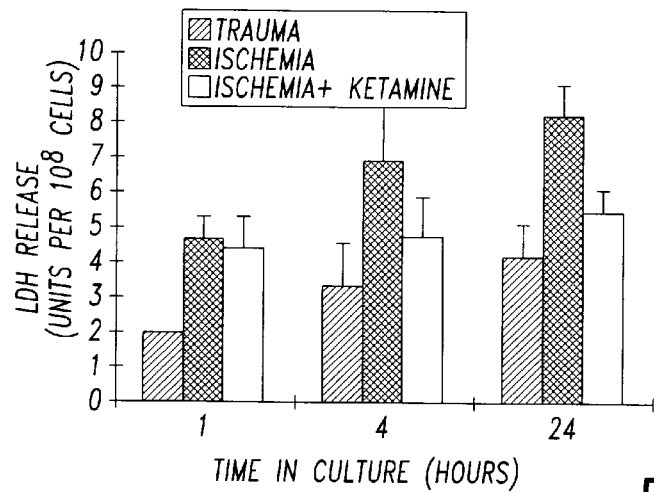
FIG. 1 is a bar graph of LDH release by retinal tissue exposed to trauma or ischemia. Retinal tissue from E17 embryos was exposed to trauma by the process of excising the tissue and subsequently cutting it into pieces. The tissue was organ-cultured for 24 hours and LDH release was measured in samples of the culture medium 1, 4 and 24 hours after tissue excision (bars with diagonal lines). E17 retina was exposed to ischemia by organ-culturing the tissue pieces for 50 minutes in glucose-free medium in flasks that were gassed with 95% $N_2$/5% $CO_2$ (cross-hatched bars). In some experiments, the culture medium of the ischemic tissue contained the glutamate antagonist ketamine (10 mM/ml) (open bars). The levels of LDH were measured in medium samples 1, 4 and 24 hours after tissue excision. Each bar represents the mean+/−SD of three separate experiments each performed in triplicate (n=9).

The present invention provides a pharmaceutical composition for treating injury to or diseases which result in neuronal degeneration resulting from stroke, brain, retina or spinal cord injuries, ischemia and reperfusion, and other brain or retinal disorders and possible trauma associated with neurosurgical procedures. Other brain disorders can include, but are not limited to, Huntington's disease (HD), Alzheimer's disease (AD), epilepsy, lathyrism, amyotrophic lateral sclerosis (ALS), Parkinsonian dementia of Guam or any other brain disorder in which glutamate-associated neuronal degeneration is implicated.

The composition consists of glutamine synthetase (GS), analogues and derivatives thereof and a pharmaceutical carrier. The derivatives of GS are preferably pharmaceutically acceptable salts and esters of GS.

The enzyme glutamine synthetase catalyzes the amidation of glutamate into the non-toxic amino acid glutamine and can thus terminate the neurotransmitter signal and prevent the cascade leading to neurotoxicity as described herein above.

An analogue will be generally at least 70% homologous over any portion that is functionally relevant. In more preferred embodiments the homology will be at least 80% and can approach 95% homology to the glutamine synthetase sequence. The amino acid sequence of an analog may differ from that of the glutamine synthetase protein when at least one residue is deleted, inserted or substituted, but the protein remains functional. Differences in glycosylation can provide analogues. The molecular weight of a glycoprotein can vary between the analogue and the present invention due to carbohydrate differences.

The present invention also provides a method for treating injury to, or diseases which, result in neuronal degeneration by administering to a patient an effective dose of glutamine synthetase, analogues and derivatives thereof. The effective dose will slow the neuronal degeneration as compared to the progress of degeneration in an untreated patient. The method can be used in both the peripheral nervous system and in the central nervous system. The present invention can also be administered in combination with glucocorticoids.

The method of the present invention also embodies preventing neuronal degeneration during neurosurgical procedures by administering a prophylaxic supply of glucocorticoids generally within 48 hours of surgery. As discussed herein below, the endogenous GS gene contains a glucocorticoid-response element in its regulatory region [Zhang and Young, 1991; Ben Dror et al., 1993]; thus, glucocorticoids directly stimulate transcription of the gene [Vardimon et al., 1988]. Therefore the glucocorticoids should be supplied prior to surgery to allow enough time for the GS gene to be activated.

The glutamine synthetase and/or glucocorticoid is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the glutamine synthetase and/or glucocorticoid can be administered in various ways, particularly since glucocorticoids can cross the blood-brain barrier. It should be noted that the glutamine synthetase and/or glucocorticoid can be administered as the compound or as pharmaceutically acceptable derivative (salt or ester) and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, and intranasal administration as well as intrathecal and infusion techniques depending on dosing requirements and other factors known to those skilled in the art. Implants of the compounds are also useful. The patient being treated is a warm-blooded animal and, in particular, mammals including man.

When administering parenterally, the glutamine synthetase and/or glucocorticoid will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. No. 5,225,182; U.S. Pat. No. 5,169,383; U.S. Pat. No. 5,167,616; U.S. Pat. No. 4,959,217; U.S. Pat. No. 4,487,603; U.S. Pat. No. 4,486,194; U.S. Pat. No. 4,447,233; U.S. Pat. No. 4,447,224; U.S. Pat. No. 4,439,196; and U.S. Pat. No. 4,475,196. Many other such implants, delivery systems, and modules are well known to those skilled in the art.

A pharmacological formulation of the glutamine synthetase and/or glucocorticoid utilized in the present invention can be administered orally to the patient. Conventional methods such as administering the compounds in tablets, suspensions, solutions, emulsions, capsules, powders, syrups and the like are usable.

Known techniques which deliver the glutamine synthetase and/or glucocorticoid orally, subcutaneously or parenterally including intravenous, intraarterial, intramuscular, intraperitoneally, and intranasal administration as well as intrathecal and infusion techniques and retain the biological activity are preferred.

For delivery within the CNS intrathecal delivery can be used with for example an Ommaya reservoir. U.S. Pat. No. 5,455,044 provides for use of a dispersion system for CNS delivery or see U.S. Pat. No. 5,558,852 for a discussion of CNS delivery. While it is known that glucocorticoids can cross the blood brain barrier, pharmacological formulations that cross the blood-brain barrier can be prepared taking advantage of this and other methods and the composition administered. [Betz et al., 1994; Brem et a;., 1993]. Such formulations can take advantage of methods now available to produce chimeric peptides in which the present invention is coupled to a brain transport vector allowing transportation across the barrier. [Pardridge, et al., 1992; Pardridge, 1992; Bickel, et al., 1993] or methods of gene therapy [Kramer et al., 1995]. Alternatively, direct infusion into the cerebral spinal fluid can also be undertaken (Wilkins and Rengachary). Additionally, blood-brain-barrier disruption may be used in appropriate cases [Neuwelt et al., 1980].

In one embodiment, the glutamine synthetase or glucocorticoid can be administered initially by intravenous injection to bring blood levels to a suitable level. The patient's glutamine synthetase or glucocorticoid levels are then maintained by an oral dosage form, although other forms of administration, dependent upon the patient's condition and as indicated above, can be used. The quantity of glutamine synthetase or glucocorticoid to be administered will vary for the patient being treated and will vary from about 100 ng/kg of body weight to 100 mg/kg of body weight per day and preferably will be from 10 μg/kg to 10 mg/kg per day.

It is to be noted, that in the case of head injury (brain injury) that the blood brain barrier is generally "breached" in the area of the trauma and the compositions of the present invention can also be administered at the site of injury thereby delivering them directly to the site.

Alternatively, gene therapy utilizing the gene for glutamine synthetase can be employed with protocols that are known to those skilled in the art. The present invention provides a method of gene therapy for treating diseases which result in neuronal degeneration due to glutamate mediated cellular damage and death by administering the gene for glutamate synthetase so that glutamate synthetase is produced in situ where it is needed to counteract the disease process. For example, pre-engineered T lymphocytes that contain the cloned glutamine synthetase gene under a strong promoter and that overexpress therefore, the glutamine synthetase enzyme, can be used to deliver the enzyme to the neural tissue [Kramer et al., 1995]. The diseases contemplated by the present invention that are due to glutamate mediated cellular damage and death include, but are not limited to, are Huntington's disease (HD), Alzheimer's disease (AD), epilepsy, lathyrism, amyotrophic lateral sclerosis (ALS) and Parkinsonian dementia of Guam.

The present invention provides for gene therapy utilizing vectors comprising an expression control sequence operatively linked to the nucleic acid sequence (Accession number Y00387) of the glutamine synthetase gene [Gibbs et al, 1987; Van der Hoff et al., 1991] that can be used therapeutically.

Vectors are known or can be constructed by those skilled in the art and should contain all expression elements necessary to achieve the desired transcription of the sequences. In particular, see the methods set forth in U.S. Pat. No. 4,866,042 to Neuwelt issued Sep. 12, 1989 titled "Method for the delivery of genetic material across the blood brain barrier" incorporated herein by reference.

The vectors can be introduced into cells or tissues by any one of a variety of known methods within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., *Gene Targeting*, CRC Press, Ann Arbor, Mich. (1995), *Vectors: A Survey of Molecular Cloning Vectors and Their Uses*, Butterworths, Boston, Mass. (1988) and Gilboa et al (1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

Recombinant viral vectors are another example of vectors useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on desired cell type to be targeted. For example, if neural cells are to be treated, then a vector specific for such neural cells will be used. Alternatively, cells can be transformed that "home" to the central nervous system.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

If viral vectors are used, for example, the procedure can take advantage of their target specificity and consequently, do not have to be administered locally at the diseased site. However, local administration may provide a quicker and more effective treatment, administration can also be performed by, for example, intravenous or subcutaneous injection into the subject. Injection of the viral vectors into a spinal fluid can also be used as a mode of administration, especially in the case of neurodegenerative diseases. Following injection, the viral vectors will circulate until they recognize host cells with the appropriate target specificity for infection.

Transfection vehicles such as liposomes can also be used to introduce the non-viral vectors described above into recipient cells within the inoculated area. Such transfection vehicles are known by one skilled within the art.

As a basis of the invention disclosed herein, Applicants have demonstrated that the process of damage amplification (cascade) in neuronal degeneration as described herein above in the Background section, which is mediated by glutamate, can be terminated by the enzyme glutamine synthetase (GS). This enzyme is part of the endogenous "buffering mechanism" which amidates the excitotoxic amino acid glutamate to the non-toxic amino acid glutamine [Waniewski and Martin, 1986]. Applicants results demonstrate that overexpression of GS, in response to hormonal induction, or supply of the purified enzyme can markedly reduce the extent of neuronal cell death.

In normal conditions, neurotoxicity of glutamate is prevented by a "buffering mechanism" in which the enzyme GS plays a key role. This enzyme catalyzes the amidation of glutamate into the 'non-toxic' amino acid glutamine and thus terminates the neurotransmitter signal and prevents neurotoxicity [Waniewski and Martin, 1986]. While the action of this "buffering mechanism" can effectively prevent neurotoxicity in normal conditions, it is apparently not capable of catalyzing the excessive amounts of glutamate released in brain trauma. This biochemical pathway led applicants to examine whether elevation of GS expression will reduce the extent of neuronal degeneration. Applicants results as shown in the Examples herein below demonstrate that this is indeed the case. Applicants offer a new conceptual approach for controlling glutamate mediated neuronal degeneration and thus open a novel avenue for therapy.

The retina is an "exteriorized" extension of the brain and can be considered a model system of neuronal tissue. The neural retina of chicken embryo offers important advantages for the study of general principles of neurophysiology and neuropathology since the tissue can be obtained in convenient amounts and can be cultured in vitro as an intact sheet of organized tissue for prolonged periods to time. Glutamate is a retinal neurotransmitter used by photoreceptors, bipolar cells and ganglion cells. Retinal ischemia has been shown to cause a large increase in the release of glutamate [Neal et al., 1994; Louzada, Jr. et al., 1992], and to result in tissue damage. This ischemic insult is prevented by administration of glutamate antagonists [David et al., 1988; Olney, 1994b; Zeevalk et al., 1989; Bracken et al., 1990], suggesting that glutamate release during ischemia is responsible for cell death.

Applicants laboratory has extensively studied various molecular aspects of chick retinal development and has explored the molecular basis for GS control. Applicants have demonstrated that the developmental increase in GS expression is controlled by systemic glucocorticoids and that a precocious supply of the hormone will induce a marked increase in GS expression [Vardimon et al., 1986]. Applicants have also shown that the GS gene contains a glucocorticoid response element (GRE) and that glucocorticoids directly stimulate the transcription of the gene [Ben Dror et al., 1993; Zhang and Young, 1991; Vardimon et al., 1988]. Expression of the glucocorticoid receptor is restricted to Muller glial cells, which are the only cells in the retinal tissue that express GS (Linser and Moscona, 1979; Grossman et al., 1994; Gorovits et al., 1994]. The ability to induce an increase in GS expression by glucocorticoids [Moscona, 1983; Vardimon et al., 1986; Patejunas and Young, 1987; Berko Flint et al., 1994] provides a tool to examine whether the GS enzyme can prevent or at least restrict neuronal damage. The ability of glucocorticoids to modulate GS expression in the retinal tissue therefore provides an important means of examining the role of GS in neuroprotection. Retinal tissue is also an established paradigm for glutamate neurotoxicity: (1) Glutamate serves as a neurotransmitter in photoreceptors, bipolar cells and ganglion cells [Massey, 1990]. (2) Insult leads to accumulation of relatively high levels of glutamate in the extracellular fluid [Louzada Junior et al., 1992; Neal et al., 1994]. (3) Administration of glutamate leads to neuronal cell death [David et al., 1988; Zeevalk, et al., 1989; Zeevalk and Nicklas, 1990]. (4) Glutamate receptor antagonists can protect against neuronal degeneration [Mosinger et al, 1991].

Applicants show in the Examples herein below that induction of GS expression in retinal tissue prevents neuronal degeneration. GS expression was induced by injecting glucocorticoids into fertilized eggs or by adding the hormone to explants of retinal tissue in organ culture. Tissue explants were subjected to ischemic conditions (glucose-free Krebs-bicarbonate medium gassed with $N_2/CO_2$) and the extent of neuronal cell death was monitored by measurement of the lactate dehydrogenase (LDH) activity released into the medium, DNA fragmentation and by analysis of histological sections. Applicants found that there is an inverse correlation between the level of GS expression and the extent of neuronal cell death. Induction of a high level of GS causes a 50–70% decline in neuronal cell death. In contrast, a supply of methionine sulfoximine (an irreversible inhibitor of GS) to the hormone treated tissue results in an increase in neuronal degeneration.

Induction of GS expression by glucocorticoids is regulated at the transcriptional level. The increase in the level of GS enzyme is relatively slow and it reaches its maximum only after 48 hours. Therefore, maximal protection (50–70%) against neuronal cell death was obtained when the hormone was supplied 48 hours prior to insult. The present invention shows that prophylaxis supply of glucocorticoids will be of great value for neuroprotection in planned surgery of the brain, retina and spinal cord.

The ability of glucocorticoids, such as cortisol, to induce GS expression and protect against neuronal degeneration might be directly related to findings obtained in a recent clinical trial. It was demonstrated that treatment with high doses of glucocorticoid (methylprednisoline) improves neurological recovery of patients with acute spinal cord injury [Bracken et al., 1990]. Early treatment (within the first 8 hours of injury) was essential for the beneficial effect. Similar results were also obtained in animal models of spinal cord and brain injury [Hall, 1985; Braughler et al., 1987], as well as after retinal photic injury [Rosner et al., 1992a, 1992b]. The molecular mechanism underlying these effects is not known. However, on the basis of the results presented in this study, Applicants propose that neurological recovery might be due, at least in part, to induction of GS expression in the injured tissue.

Applicants results highlight some potential weaknesses of glucocorticoid treatment post-trauma. Induction of GS expression by glucocorticoids is a time-consuming process. Glucocorticoids regulate GS expression by stimulating transcription of the gene, and it takes about 24 hours to obtain a significant increase in the enzyme itself. This might explain why glucocorticoids must be supplied early in order to achieve a beneficial effect and suggest that in planned neurological interventions prophylactic administration of glucocorticoids might be advisable. Hormonal induction of GS expression might also depend on particular physiological conditions. Applicants and others have demonstrated, for example, that GS induction is dependent on cell to cell contacts between glia and neurons [Linser and Moscona, 1983; Vardimon et al., 1988; Reisfeld and Vardimon, 1994]. Thus, the extent of GS induction in an injured tissue might depend on the severity of the insult and on its anatomical location.

In the case of stroke and brain or spinal cord injuries, when glucocorticoids cannot be supplied in advance another approach must be taken. The finding hat the purified enzyme can protect against neuronal degeneration offers a way to circumvent these obstacles and open new avenues for medical therapy. The purified enzyme appears to provide rapid and massive protection against neuronal cell degeneration.

The results of the Example herein below demonstrate that GS markedly reduces the extent of neuronal degeneration in retinal tissue following its exposure to trauma or ischemia. This enzyme is part of an endogenous mechanism that prevents the accumulation of synaptically released glutamate in the extracellular fluid. Trauma or ischemia caused extensive cell degeneration in the retinal tissue, which could be assessed in terms of LDH efflux, DNA fragmentation and histological appearance. The protective effect of ketamine, as well as of other glutamate antagonists [Mosinger et al., 1991], point to the involvement of glutamate neurotoxicity in this process. Elevation of GS by hormonal induction of the endogenous gene or by exogenous supply of the purified enzyme protects against neuronal degeneration. The beneficial effect of elevated GS appears to be relate to the ability of the enzyme to catalyze the amidation of glutamate to the nontoxic glutamine, since inhibition of GS activity by MSO caused an increase in cell death.

Under normal conditions, amidation of glutamate to glutamine occurs in glial cells, which are the only cells in the retinal tissue that express GS. This might be the case in injured tissue as well. Glutamate is transported into glia and is converted by GS to glutamine, which is subsequently exported from the cells. The increase in GS expression as a consequence of hormonal induction might cause an accelerated transport of postsynaptic glutamate into glia and thus protect against neurotoxicity. Alternatively, in injured tissue, GS might catalyze the conversion of glutamate to glutamine not only intracellularly but also, or perhaps predominantly, outside the cells. Trauma or ischemia might damage glial cells and trigger the release of active GS into the extracellular fluid so that the enzyme can act directly on postsynaptic glutamate. Hormonal induction of GS expression results in more abundant availability of GS in the postsynaptic space, providing better protection against glutamate neurotoxicity as shown by Applicants finding that purified GS can exert its protective activity in the extracellular fluid.

The purified enzyme, which consists of eight subunits and has a molecular weight of 340,000 daltons [Rowe et al., 1970], probably remains in the extracellular milieu when injected into a fertilized egg or added to the culture medium of retinal tissue. Nevertheless, its protective activity is as efficient as that of the endogenously induced enzyme.

Also of relevance is Applicants recent finding that GS activity can be detected in the culture medium of injured retina. The level of GS in the culture medium is proportional (about 2%) to that found in the tissue, suggesting that following injury the damaged glial cells release GS into the extracellular fluid.

These findings support the hypothesis that in injured tissue GS can exert its protective activity in the postsynaptic space. Interestingly, in advanced stages of Alzheimer's disease, this enzyme can be detected in the cerebrospinal fluid [Gunnersen and Haley, 1992]. In some, in vivo injury paradigms neuronal degeneration is accompanied by an increase in astrocyte GS [Norenberg, 1982; Sandberg et al., 1985; Tanaka et al., 1992; Petito et al., 1992]. This increase has been attributed to reactive astrocytosis that occurs in response to neural insults and might be part of an endogenous mechanism for neuroprotection.

The above discussion provides a factual basis for the use of glutamine synthetase (GS) in treating or preventing neuronal degeneration. The methods used with and the utility of the present invention can be shown by the following non-limiting examples and accompanying figures.

EXAMPLES

METHODS

Tissue preparation and treatment: Retinas were isolated under sterile conditions from chicken embryos (White Leghorn) at days 15 to 17 of embryonic development (E15–E17). This tissue was placed in CMF buffer (137 mM NaCl, 2.7 mM KCl, 8 mM $Na_2HPO_4$, 1 mM $KH_2PO_4$, 5.5 mM Glucose) and cut into pieces of about 10 sq. mm. This process of tissue insult was termed trauma. The tissue pieces were cultured in 25-ml Erlenmeyer flasks, one retina per flask, in 3 ml Krebs medium (118 mM NaCl, 4.8 mM KCl, 2.4 mM $CaCl_2$, 1.2 mM $KH_2PO_4$, 1.2 mM $MgSO_4$, 1.2 mM glucose, $NaHCO_3$, pH 7.4). The flasks were gassed with 95% air/5% $CO_2$, sealed and incubated on a gyratory shaker (65 rpm) at 38° C. To simulate exposure of the tissue to ischemic conditions, the retinal pieces were cultured in glucose-free Krebs medium in Erlenmeyer flasks that were gassed for 50 minutes with $N_2$. After the first hour of incubation, the Krebs medium in tissues exposed to trauma and to ischemia was replaced by serum-free Bio-MPM medium (Biological Industries, Israel). The flasks were gassed with 95% air/5% $CO_2$, sealed and incubated on a gyratory shaker for a further 3 to 48 hours. After 24 hours, the medium was changed again. Medium samples were collected for LDH analysis.

To induce GS expression in the organ-cultured retina, cortisol (Sigma Chemical Co., St. Louis, Mo.) was added to the medium to a final concentration of 0.33 $\mu$g/ml. GS expression in ovo was induced by injecting 0.001 to 2 mg hydrocortisone 21-phosphate (Sigma Chemical Co.), dissolved in 0.1 ml distilled water, extraembryonically into the amniotic cavity by using a 25-gauge needle that was inserted through the shell at the blunt end of the egg. The shell was sealed with cellophane tape and the eggs were incubated for additional 24 or 48 hours before the retina was excised. In some experiments, L-methionine sulfoximine (MSO) (Sigma Chemical Co), a specific GS inhibitor, or DL-buthionine-[S,R]-sulfoximine (Sigma Chemical Co., St.

Louis, Mo.), a close derivative that was used as a control, were co-injected (1 mg in 0.1 ml distilled water per egg).

Supply of purified GS enzyme: GS, purified from sheep brain (Sigma Chemical Co.), was stabilized in a lipid environment before use. Briefly, L-alpha-phosphatidylcholine Type IIS from soybean (Sigma Chemical Co.) was dispersed in distilled water at an initial concentration of 20 mg/ml, briefly sonicated and subjected to centrifugation at 10,000 g for 5 minutes. The supernatant was collected and used to prepare stock solutions of the GS enzyme for addition to the culture medium or injection into fertilized eggs at a dilution of 1:10. The enzyme (100 μl) was injected extraembryonically into the amniotic cavity by inserting a 25-gauge needle through the shell at the blunt end of the egg. To inject the enzyme behind the eyeball, a window 25 mm in diameter was cut in the shell at the blunt end and the enzyme was injected (50 μl) using a 25-gauge needle. Control eggs were injected with carrier. The shell was sealed with cellophane tape and the eggs were incubated for additional 24 or 48 hours before the retina was excised.

LDH and GS assays: Neuronal degeneration was quantitatively assessed by measurement of LDH release into the culture medium, as described previously [Koh and Choi, 1987]. Briefly, samples of culture medium (25 μl) were added to freshly prepared LDH substrate buffer (0.76 mM sodium pyruvate, 85 μM NADH in 0.1M $KH_2PO_4$ buffer, pH 7.5) at room temperature. Absorbance of the reaction mixture at 340 nm was measured with a spectrophotometer for 1 minute and the amount of LDH released by a single retina ($10^8$ cells) was calculated in units from the slope of the absorbance curve. One unit is the amount of LDH that will cause a decrease of 0.001 per minute in the absorbance of a 1 ml reaction mixture. Since the culture medium was changed after the first hour of incubation, the amount of LDH measured in the discarded medium was added to the amount of LDH release at later time points. GS activity was measured in tissue sonicates as previously described [Moscona et al, 1968]. Its specific activity was expressed as micromoles of gamma-glutamylhydroxamate (GHA) per hour per milligram of protein.

Quantitation of DNA fragmentation: DNA fragmentation was assayed using the method of Brune et al. [Brune et al, 1991]. Retinal tissue was washed in CMF buffer and homogenized by ten strokes with pestle A and ten strokes with pestle B in a Dounce homogenizer in cold lysis buffer [20 mM EDTA, 0.5% (v/v) Triton X-100, and 5 mM Tris-Cl, pH 7.4]. The homogenate was incubated for 15 minutes on ice prior to centrifugation for 15 minutes at 27,000 g to separate intact chromatin (pellet) from DNA fragments (supernatant). Fragmented DNA was extracted twice with phenol chloroform, precipitated overnight with 2 volumes of ice-cold ethanol at −20° C., washed with 70% ethanol, air-dried, and resuspended in TE buffer (10 mM Tris-HCl, 1 mM EDTA, pH 8.0). DNA samples, each prepared from an equal number of cells, were fractionated by electrophoresis in 1.8% agarose gels. The gels were stained with ethidium bromide, visualized by ultraviolet (UV) light and photographed. DNA fragmentation was quantitated by densitometric scanning of the pictures.

Histology and immunohistochemistry: E17 retinas excised from treated or untreated eggs were fixed with Carnoy's fixative and embedded in paraffin either immediately after excision or after being cultured for 4 hours. Paraffin sections (5 μm) were stained either with hematoxylin/eosin or by the indirect immunofluorescence method. For immunofluorescence, sections were stained with rabbit anti-glutamine synthetase antiserum (kindly provided by A. A. Moscona, University of Chicago, Chicago) and then with fluorescein-conjugated anti-rabbit antibodies (Sigma Chemical Co.). Antibody binding was detected by immunofluorescence with epi-illumination from a UV source.

Results

Neuronal degeneration in embryonic retinal tissue: Excision of retinal tissue from E17 embryos and subsequent cutting of the tissue into pieces injured many cells and caused substantial cell death. This trauma was manifested by a massive release of lactate dehydrogenase (LDH) into the culture medium, which increased progressively with time (FIG. 1A). LDH efflux, shown to be a quantitative measure of the extent of neuronal degeneration [Koh and Choi, 1987], increased even further upon exposure of the tissue to ischemic conditions. Addition of ketamine, an NMDA-receptor antagonist, caused a decline in LDH release. These findings are in agreement with previous observations suggesting that insult-induced retinal cell degeneration is mediated by glutamate [Mosinger et al., 1991].

Figure 2A:
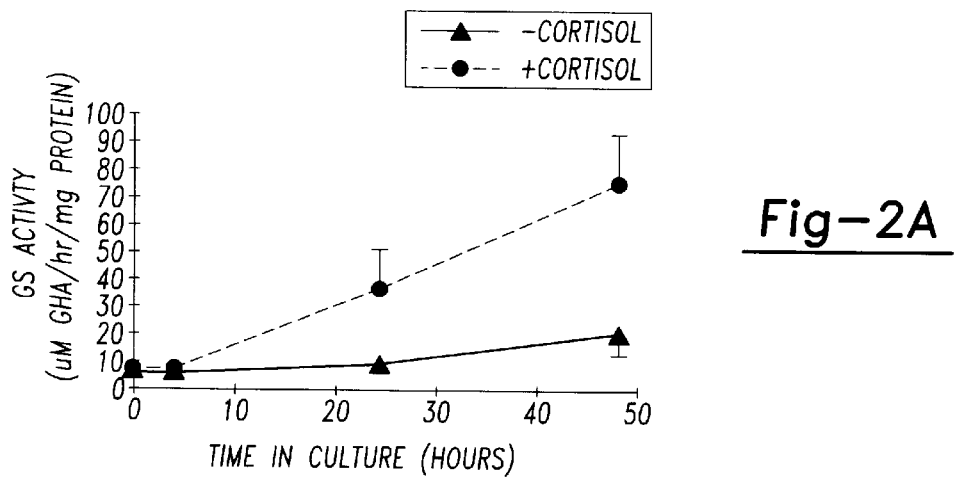
FIGS. 2A–B are graphs showing that the addition of cortisol at the time of insult does not affect LDH release. Retinal tissue, excised from E16 embryos, was cut into pieces and organ-cultured in the presence (dotted line) or absence (continuous line) of cortisol (0.33 μg/ml). The levels of GS in the tissue (a) and of LDH in the culture medium (B) were measured immediately or 4, 24 and 48 hours after tissue excision. The results are means+/−SD of two independent experiments, each performed in triplicate (n=6).
Figure 2B:
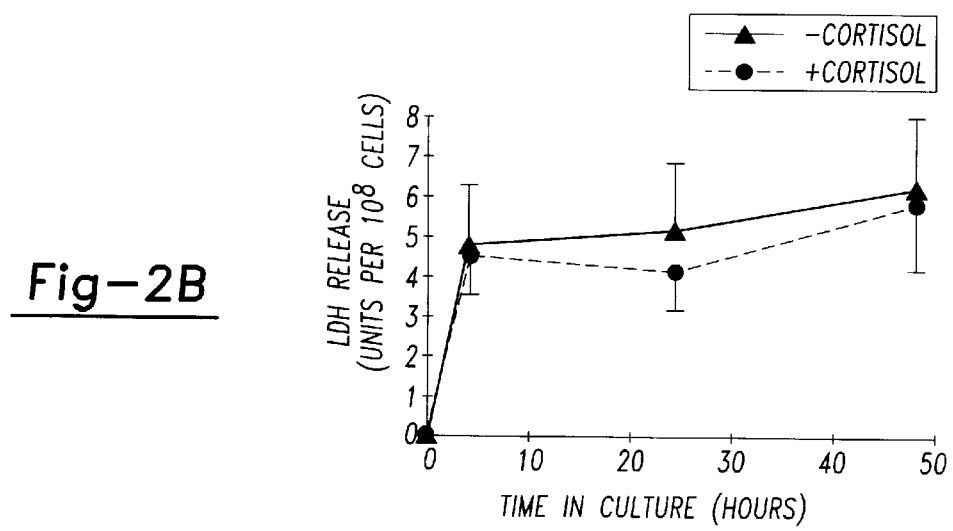

Induction of GS expression by glucocorticoids protects against neuronal degeneration: All of the experiments described herein below were carried out with retinal tissues exposed to both trauma and ischemia. Since the results were quite similar, Applicants present here only those obtained with traumatized tissue. In order to examine the ability of GS to protect against neuronal degeneration, Applicants used the glucocorticoid hormone, cortisol, to induce a high level of GS in the retinal tissue. Addition of cortisol to explants of retinal tissue did not induce any increase in GS activity within the first 4 hours. Cortisol induced a high level of GS activity within 24 hours and the level increased further between 24 and 48 hours (FIG. 2A). In contrast, the release of LDH by retinal explants was already substantial 4 hours after tissue excision (FIG. 2B). It was, therefore, not surprising that under these experimental conditions, in which degeneration of retinal cells preceded the increase in GS expression, addition of cortisol did not cause a significant change in LDH efflux (FIG. 2B).

Figure 3A:
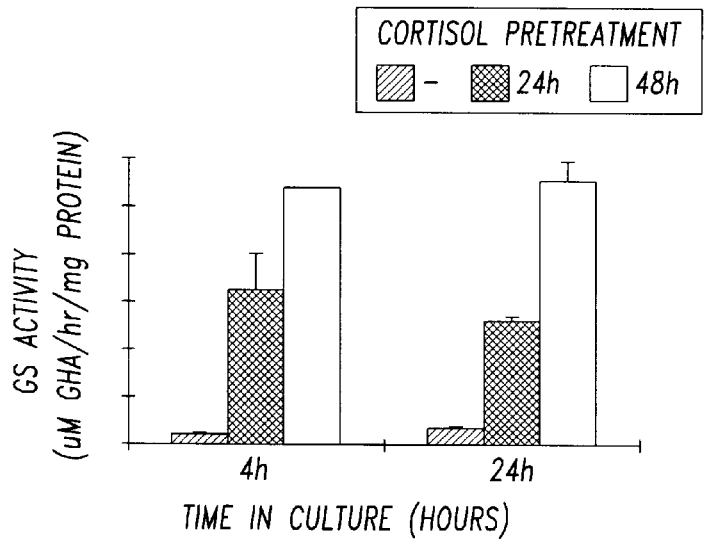
FIGS. 3A–C are bar graphs showing that addition of cortisol prior to insult causes a decline in LDH release. Cortisol (1 mg per egg) was injected into E15 (open bars) or E16 (crosshatched bars) eggs, which were then incubated for an additional 48 or 24 hours, respectively. Control eggs were injected with carrier (bars with diagonal lines). Retinal tissue was excised, cut into pieces and organ-cultured for 24 hours. The levels of GS in the tissue (A) and of LDH in the culture medium (B) were measured 4 and 24 hours after tissue excision. The difference of LDH release between the cortisol-treated and untreated tissue was calculated as a percentage of LDH release in the untreated tissue (C). Each bar represents the mean+/−SD of three separate experiments, each performed in duplicate (n=6).
Figure 3B:
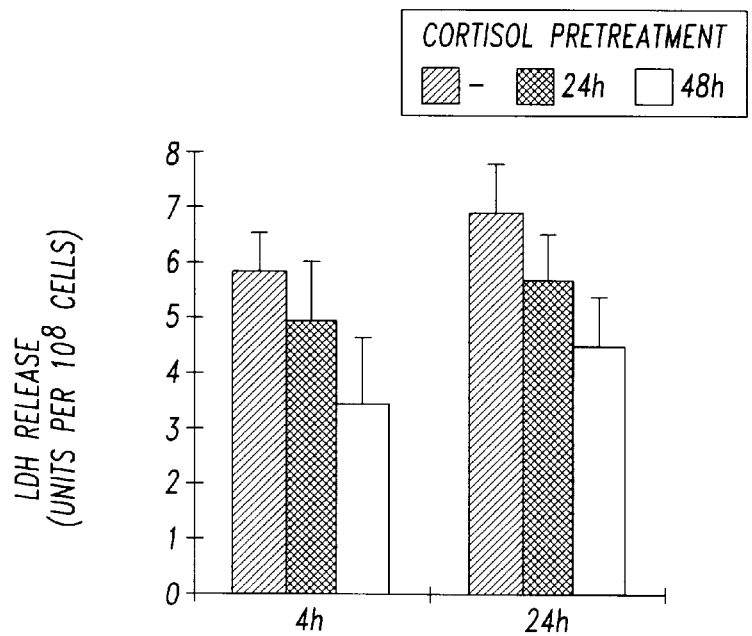
Figure 3C:
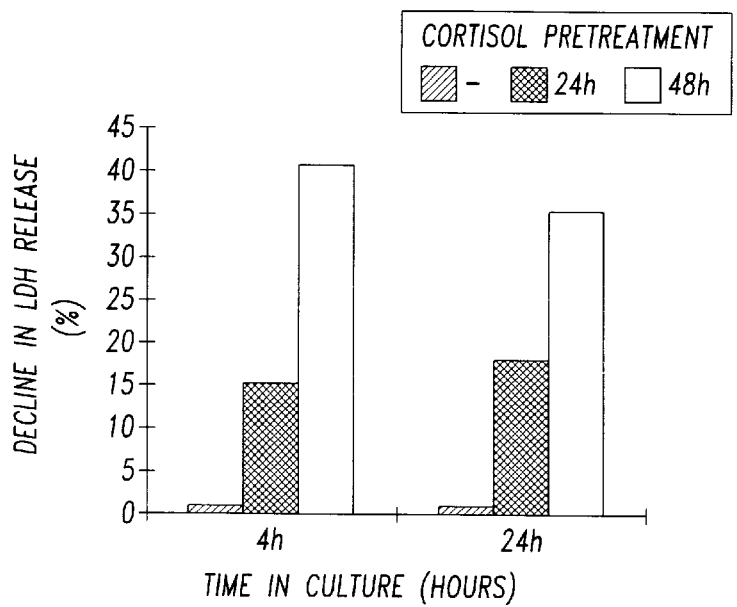
Figure 4:
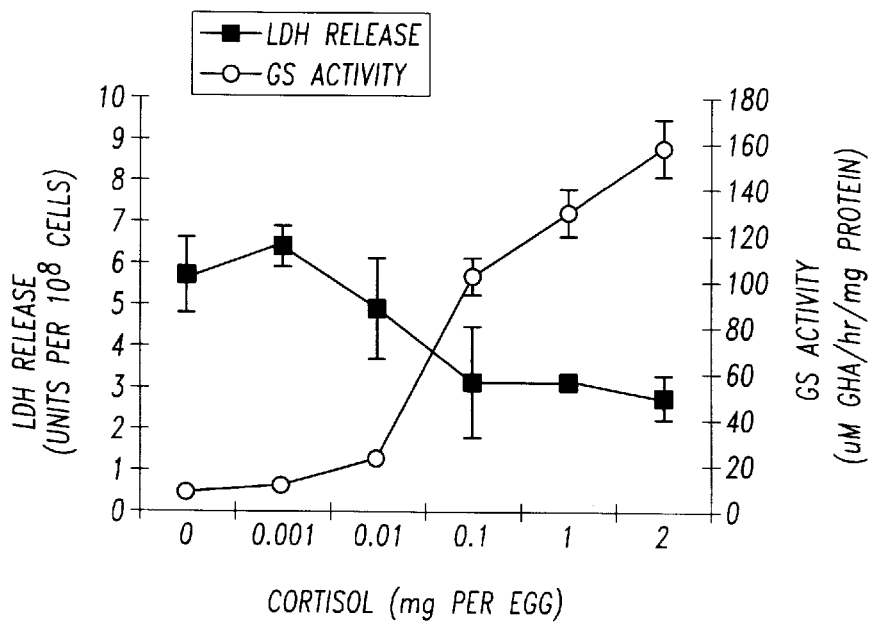
FIG. 4 is a graph which shows the inverse correlation between GS induction and LDH release. E15 eggs were injected with cortisol in the indicated amounts and incubated for an additional 48 hours. Retinal tissues were excised, cut into pieces and organ-cultured for 4 hours. The level of GS in the tissue (white circles) and of LDH in the culture medium (black boxes) was measured. Results are means+/−SD of three independent experiments, each performed in duplicate (n=6).

In order to obtain a high level of GS in the retina at the time of insult, cortisol was supplied prior to tissue excision. E15 or E16 eggs were injected with cortisol and incubated for an additional 48 or 24 hours, respectively, before the retina was excised. Supply of cortisol to the embryo 48 hours prior to insult resulted in a 15-fold increase in GS activity and a 35–40% decline in LDH release; supply of cortisol 24 hours prior to insult induced a 7-fold increase in GS activity and a 15–18% decline in LDH release (FIG. 3). These effects were dose dependent: at low levels of cortisol GS activity was low and LDH release was high, while at higher levels of cortisol, GS activity was high and LDH release was low (FIG. 4). The inverse correlation between LDH release and GS activity shows that GS is functionally implicated in protection against neuronal degeneration.

Figure 5A:
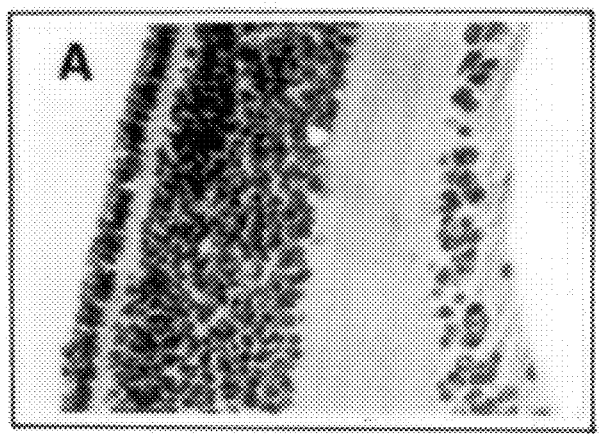
FIGS. 5A–C are photographs providing morphological evidence for cortisol protection against neuronal degeneration. E15 eggs were injected with cortisol (1 mg per egg) (A) or carrier (B) and incubated for an additional 48 hours before the retina was excised. Retinal explants were cut into pieces, organ-cultured for 4 hours and then embedded in paraffin. Untreated E17 retina was embedded immediately after excision (C). Paraffin sections were stained with hematoxylin/eosin. Bar, 20 μm.
Figure 5B:
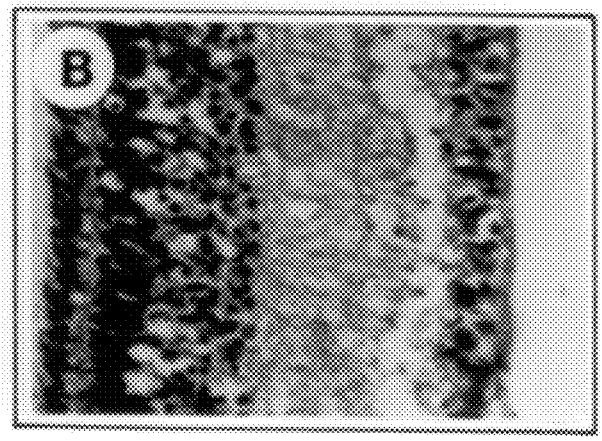
Figure 5C:
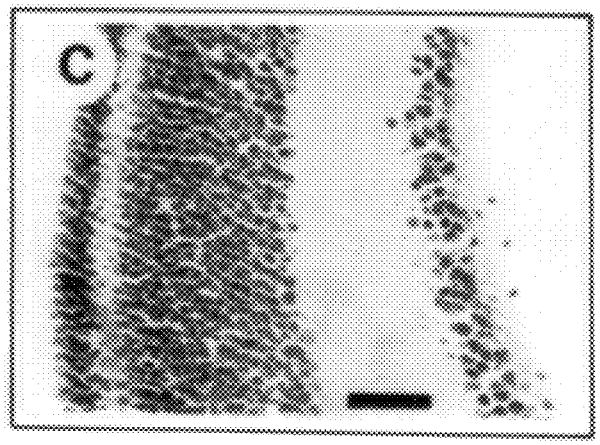

The protective effect of cortisol was also evaluated by analysis of histological sections. Traumatized tissue, 4 hours after insult, differed conspicuously in several respects (FIG. 5B) from the normal appearance of uncultured retina (FIG. 5C). The inner region of the inner nuclear layer, the inner plexiform layer and the ganglion cell layer appeared edematous and contained numerous cells with pyknotic nuclei. Addition of cortisol 48 hours prior to tissue excision prevented these pathological changes (FIG. 5A), although mild cytopathology could be observed in some of the sections.

Figure 6:
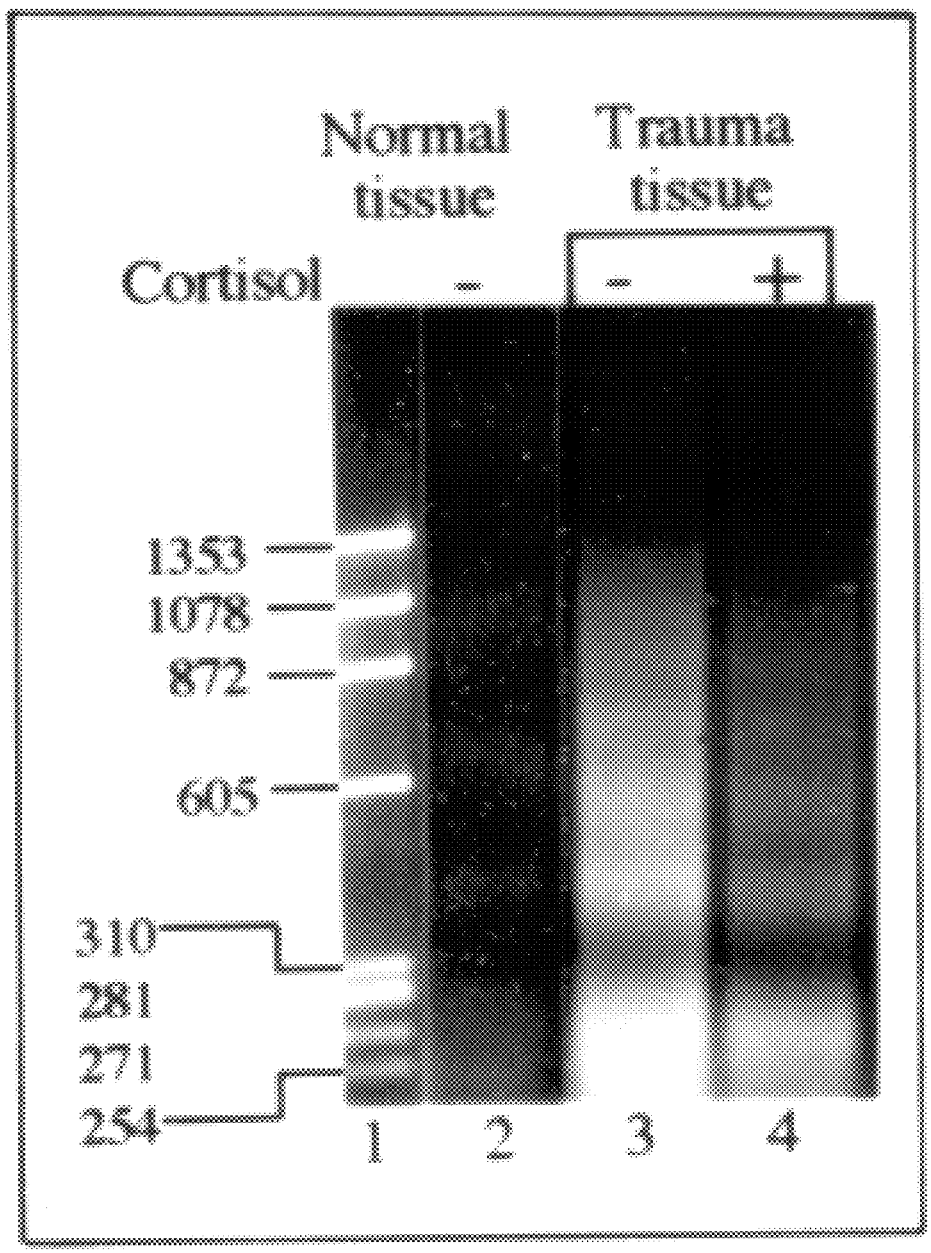
FIG. 6 is a photograph of an electrophoretic gel showing that the internucleosomal DNA fragmentation is attenuated by cortisol. E15 eggs were injected with cortisol (1 mg per egg) (lane 4) or carrier (lane 3) and incubated for an additional 48 hours before the retina was excised. Retinal explants were cut into pieces and organ-cultured for 24 hours. DNA was extracted and DNA samples from an equal number of cells ($5 \times 10^7$ cells per lane) were analyzed by gel electrophorsis and visualized with the fluorescent intercalating dye ethidium bromide. DNA was extracted from untreated E17 retina immediately after tissue excision (lane 2). Molecular weight markers are from a HaeIII digest of ΦX174 phage DNA (lane 1).

Several studies have suggested the involvement of apoptosis in insult-induced neuronal degeneration [Kure et al., 1991; Linnik et al., 1993; MacManus et al., 1993; Heron et al., 1993]. Applicants, therefore, examined whether the protective effect of cortisol could also be demonstrated by analysis of internucleosomal DNA fragmentation, a phenomenon associated with apoptosis. Internucleosomal DNA fragmentation, identified by gel electrophoresis, increased markedly upon insult (FIG. 6, lanes 1 and 2). Addition of cortisol 48 hours prior to tissue excision caused a 40% decline in the extent of DNA fragmentation (FIG. 6, lane 3). Thus, both qualitative and quantitative assessment of neuronal degeneration, by analysis of LDH efflux, histological sections and DNA fragmentation, all indicated that a cortisol-induced increase in GS expression is correlated with a decline in cell degeneration.

Figure 7:
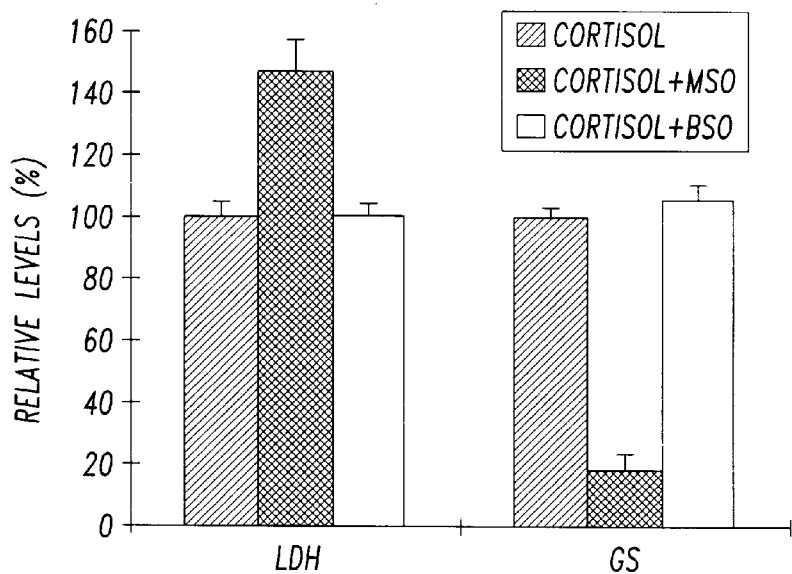
FIG. 7 is a bar graph showing inhibition of GS activity causes an increase in LDH release. E15 eggs were co-injected with cortisol (1 mg per egg) and methionine sulfoximine (MSO) (1 mg per egg) (crosshatched bar), buthionine sulfoximine (BSO) (1 mg per egg) (open bar) or carrier (bar with diagonal lines). The eggs were incubated for an additional 48 hours before the retina was excised. Retinal explants were cut into pieces and organ-cultured for 4 hours. The levels of GS in the tissue and of LDH in the culture medium were measured. Each bar represents the mean+/−SD of two separate experiments, each performed in triplicate (n=6).

Inhibition of GS activity causes an increase in neuronal degeneration: The finding of an inverse correlation between the level of GS activity and the extent of cell degeneration does not exclude the possibility that other biological activities, included or repressed by cortisol, are the direct cause of neuroprotection. To demonstrate the causative role of GS in this process, Applicants examined the effect of methionine sulfoximine (MSO), a selective inhibitor of GS activity [Ronzio et al., 1969], on the extent of neuronal degeneration. Buthionine sulfoximine (BSO), a close derivative that does not inhibit GS activity [Meister, 1986], was used as a control. As expected, MSO caused a dramatic decline in GS activity, whereas BSO did not affect it (FIG. 7). MSO-induced inhibition of GS activity caused a 50%: increase in the extent of LDH release (FIG. 7). These results demonstrate that the protective activity of cortisol is mediated, at least in part, by GS.

Figure 8A:
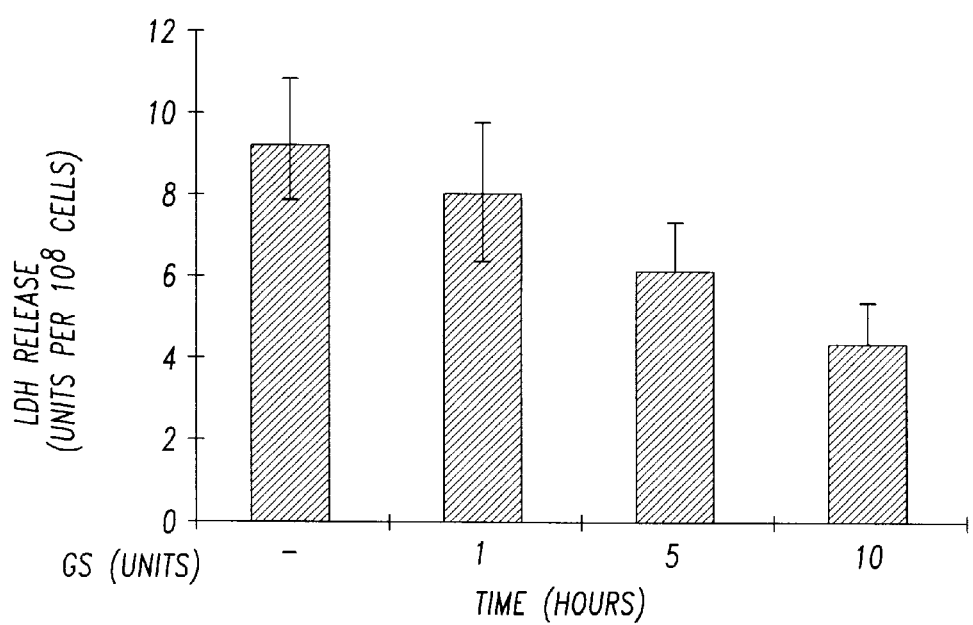
FIGS. 8A–C are bar graphs showing the supply of purified GS enzyme in vitro or in ovo reduces the extent of LDH release. (A) E17 retina was excised, cut into pieces and organ-cultured in the absence (−) or presence of purified GS enzyme in the indicated unit amounts. The level of LDH in the culture medium was measured after 4 hours. Each bar represents the mean+/−SD of two separate experiments, each performed in triplicate (n=6). (B) E17 eggs were injected with carrier (−), with purified GS enzyme in the indicated unit amounts (1 to 8 units per egg), with ovalbumin (x μg per egg) (OVA) or with x units of heat-inactivated GS enzyme (IGS). The injected eggs were incubated for 2 hours before the retina was excised. Retinal explants were cut into pieces and organ-cultured for 4 hours, and the level of LDH in the culture medium was then measured. Each bar represents the mean+/−SD of two separate experiments, each performed in quadruplicate (n=8). (C) E15, E16 and E17 eggs were injected with purified GS enzyme (2 units per egg). Retinas were excised from the injected E17 eggs immediately (−) or after 2 or 4 hours (2 h, 4 h) of incubation. Injected E16 and E15 eggs were incubated for an additional 24 or 48 hours, respectively (24 h, 48 h) before the retinal tissues were excised. Tissue explains were cut into pieces and organ-cultured for 4 hours, and the level of LDH in the culture medium was then measured. Each bar represents the mean+/−SD of two separate experiments, each performed in quadruplicate (n=8).
Figure 8B:
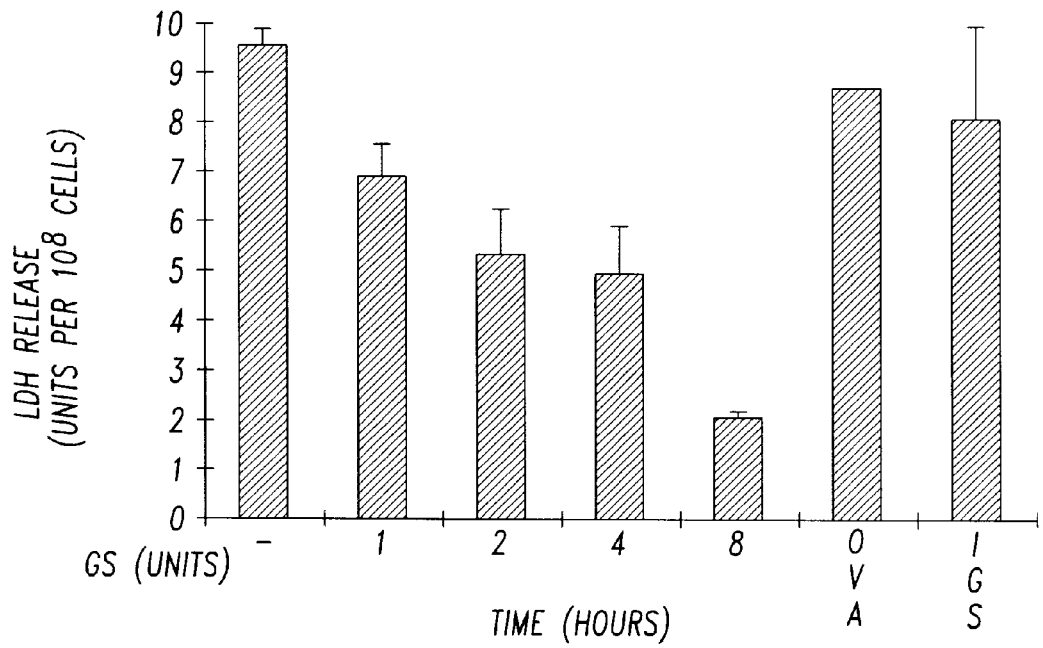
Figure 9A:
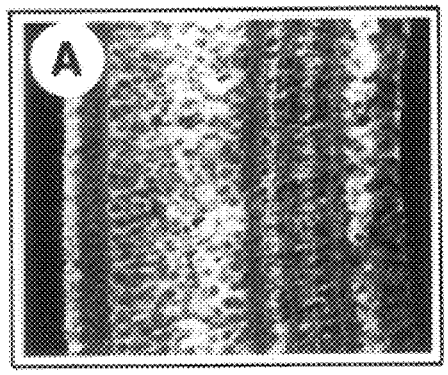
FIGS. 9A–F are photographs providing morphological evidence for protective effects of the purified GS enzyme. E17 eggs were injected with purified GS enzyme (2 units per egg) (A and D) or with carrier (B and E) and incubated for 2 hours before the retinas were excised. Retinal explants were embedded immediately after excision (A and B) or were cut into pieces, organ-cultured for 4 hours and then embedded in paraffin (D and E). Paraffin sections were stained with rabbit anti-GS-specific antiserum and with goat anti-rabbit IgG (A and B) or with hematoxylin/eosin (D and E). E15 eggs were injected with cortisol (1 mg per egg) and incubated for an additional 48 hours before the retina was excised. The excised tissue was embedded in paraffin and histological sections were stained with rabbit anti-GS-specific antiserum and with goat anti-rabbit IgG (C). Untreated E17 retina was embedded immediately after excision and stained with hematoxylin/eosin (F). Bar, 25 μm.
Figure 9B:
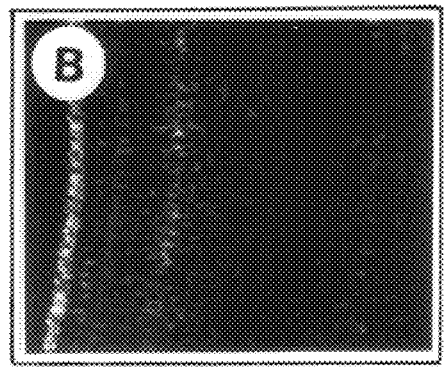
Figure 9C:
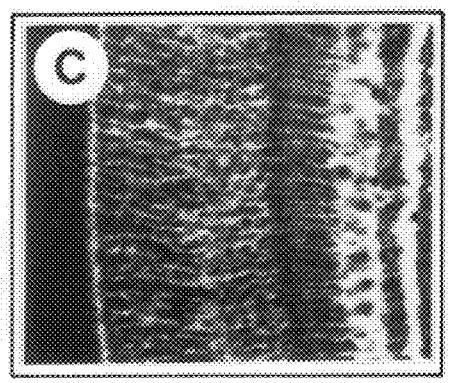

Purified GS can protect against neuronal degeneration: To demonstrate the protective effect of GS, the most direct approach is to use the purified enzyme itself. Applicants supplied increasing amounts of GS from sheep brain to the culture medium of retinal explants and measured the levels of LDH release. GS caused a dose-dependent decline in LDH release (FIG. 8A). At 10 units per retina, GS provided 50% protection against neuronal degeneration. The effect was even more dramatic when GS was supplied in ovo directly to the embryo (FIG. 8B). Immunohistochemical staining of retinal sections with anti GS antibodies (FIG. 9A) indicated that the enzyme, injected extraembryonically into the amniotic cavity or intraembryonically behind the eyeball, diffused into the retinal tissue within 1 hour. Judging from the staining intensities, GS level in retinas from enzyme-injected embryos were similar to those in cortisol-injected ones (FIG. 9C).

Figure 8C:
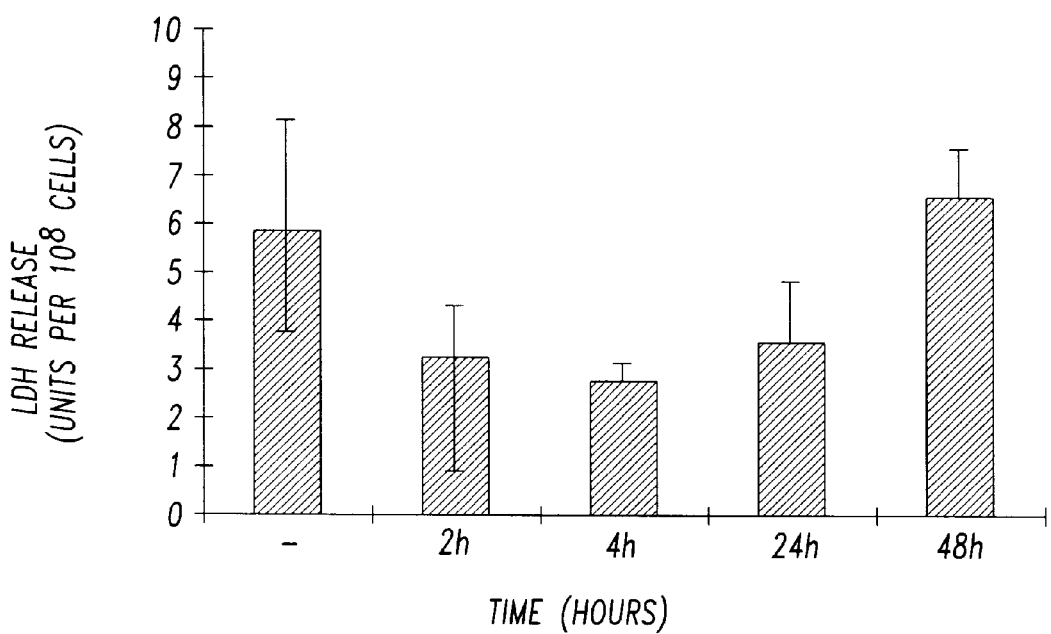

However, staining efficiency might be dependent on the cellular localization of the enzyme, which is intracellular in the case of hormonal induction and extracellular when the enzyme is supplied directly. Injection of GS caused a dose-dependent decline in LDH release, while injection of ovalbumin or of heat-inactivated GS had no effect (FIG. 8B). GS could substantially reduce the extent of LDH release if supplied 24 hours prior to insult, but lost (FIG. 8C) its protective activity between 24 and 48 hours of injection.

Figure 9D:
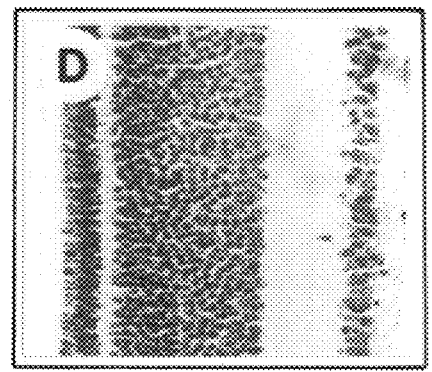
Figure 9E:
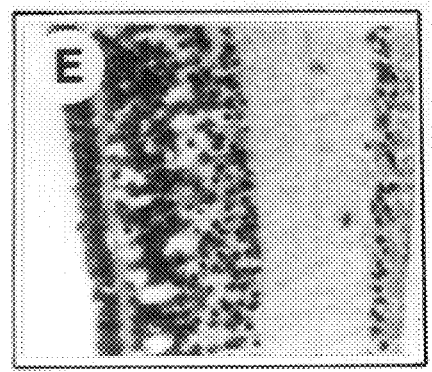
Figure 9F:
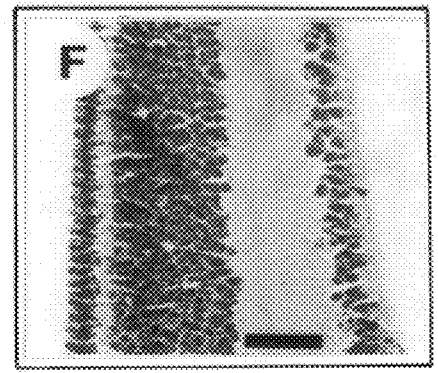

The protective effect of the injected GS could also be demonstrated by inspection of histological sections. As in the case of cortisol (FIG. 5), injection of GS 1 hour prior to insult prevented the pathological changes observed in traumatized tissue (FIGS. 9D–F), although mild cytopathology could be observed in some sections. These results clearly demonstrated that GS is an efficient neuroprotectant that can reach the retinal tissue when injected into the egg and can also exert its protective activity in the extracellular fluid.

Throughout this application, various publications, including United States patents, are referenced by first author and year for the publications or by number for the patents. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Ankarcrona et al., "Glutamate-induced neuronal death: a succession of necrosis or apoptosis depending on mitochondrial function" Neuron, 15:961–973 (1995).

Ben Dror et al., "Developmental control of glucocorticoid receptor transcriptional activity in embryonic retina" Proc. Natl. Acad. Sci. USA, 90:1117–1121 (1993).

Betz et al., 1994, Basic Neurochem. Molecular Cell, (Raven Press Ltd, NY) 5th Ed., 681–699

Berko Flint et al., "Involvement of c-Jun in the control of glucocorticoid receptor transcriptional activity during development of chicken retinal tissue" EMBO J., 13:646–654 (1994).

Bickel, et al., 1993, "Pharmacologic effects in vivo in brain by vector-mediated peptide drug delivery" Proc. Natl. Acad. Sci. USA 90(7)2618–2622

Bonfoco et al., "Apoptosis and necrosis: two distinct events induced, respectively, by mild and intense insults with N-methyl-D-aspartate or nitric oxide/superoxide in cortical cell cultures" Proc. Natl. Acad. Sci. U.S.A., 92:7162–7166 (1995).

Bracken et al., "A randomized, controlled trial of methyprednisolone or naloxone in the treatment of acute spinal-cord injury. Results of the Second National Acute Spinal Cord Injury Study" N. Engl. J. Med., 322:1405–1411 (1990).

Braughler et al., "Evaluation of an intensive methylprednisolone sodium succinate dosing regimen in experimental spinal cord injury" J. Neurosurg., 67:102–105 (1987).

Brem et al., "Polymers as controlled drug delivery devised for the treatment of malignant brain tumors" Eur. J. Pharm. Biopharm 39:2–7 (1993)

Brune et al., "Spermine prevents endonuclease activation and apoptosis in thymocytes" Exp. Cell Res. 195:323–329 (1991).

Calne et al., "Alzheimer's disease, Parkinson's disease, and motoneurone disease: abiotrophic interaction between aging and environment?" Lancet, 2:1067–1070 (1986).

Choi, "Glutamate neurotoxicity and diseases of the nervous system" Neuron, 1:623–634 (1988).

Choi, "Calcium: still center-stage in hypoxic-ischemic neuronal death" Trends. Neurosci., 18:58–60 (1995).

Choi and Rothman, "The role of glutamate neurotoxicity in hypoxic-ischemic neuronal death" Annu. Rev. Neurosci., 13:171–182 (1990).

Clifford et al., "Ketamine and MK-801 prevent degeneration of thalamic neurons injured by focal cortical seizures" Exp. Neurol., 105:272–279 (1989).

Coyle and Schwarcz, "Lesion of striatal neurons with kainic acid provides a model for Huntington's chorea" Nature, 263:244–246 (1976).

David et al., "Involvement of excitatory neurotransmitters in the damage produced in chick embryo retinas by anoxia and extracellular high potassium" Exp. Eye Res., 46:657–662 (1988).

Drejer et al., "Cellular origin of ischemia-induced glutamate release from brain tissue in vivo and in vitro" *J. Neurochem.*, 45:145–151 (1985).

Dubinsky and Rothman, "Intracellular calcium concentrations during "chemical hypoxia" and excitotoxic neuronal injury" *J. Neurosci.*, 11:2545–2551 (1991).

Dykens et al., "Mechanism of kainate toxicity to cerebellar neurons in vitro is analagous to reperfusion tissue injury" *J. Neurochem.*, 49:1222–1228 (1987).

Gibbs et al., "Sequence of a human glutamine synthetase cDNA" *Nucleic Acid Res.*, 15:6293 (1987).

Gilboa, E, Eglitis, M A, Kantoff, P W, Anderson, W F: Transfer and expression of cloned genes using retroviral vectors. BioTechniques 4(6):504–512, 1986.

Gorovits et al., "Developmental changes in the expression and compartmentalization of the glucocorticoid receptor in embryonic retina" *Proc. Natl. Acad. Sci. U.S.A.*, 91:4786–4790 (1994).

Grossman et al., "Molecular basis for differential expression of glutamine synthetase in retina glia and neurons" *Brain Res. Mol. Brain Res.*, 21:312–320 (1994).

Gunnersen and Haley, "Detection of glutamine synthetase in the cerebrospinal fluid of Alzhemier diseased patients: a potential diagnostic biochemical marker" *Proc. Natl. Acad. Sci. U.S.A.*, 89:11949–11953 (1992).

Hall, "High-dose glucocorticoid treatment improves neurological recovery in head-injured mice" *J. Neurosurg.*, 62:882–887 (1985).

Heron et al., "Regional variability in DNA fragmentation after global ischemia evidenced by combined histological and gel electrophoresis observations in the rat brain" *J. Neurochem.*, 61:1973–1976 (1993).

Koh and Choi, "Quantitative determination of glutamate mediated cortical neuronal injury in cell culture by lactate dehydrogenase efflux assay" *J. Neurosci. Methods*, 20:83–90 (1987).

Kramer et al., "Gene transfer through the blood-nerve barrier: NGF-engineered neuritogenic T lymphocytes attenuate experimental autoimmune neuritis" *Nature Medicine*, 1:1162–1166 (1995).

Kure et al., "Glutamata triggers internucleosomal DNA cleavage in neuronal cells" *Biochem. Biophys. Res. Commun.*, 179, 39–45 (1991).

Linnik et al., "Evidence supporting a role for programmed cell death in focal cerebral ischemia in rats" *Stroke*, 24:2002–2009 (1993).

Linser and Moscona, "Induction of glutamine synthetase in embryonic neural retina: localization in Muller fibers and dependence on cell interactions" *Proc. Natl. Acad. Sci. USA.*, 76:6476–6480 (1979).

Linser and Moscona, "Hormonal induction of glutamine synthetase in cultures of embryonic retina cells: requirement for neuron-glia contact interactions" *Dev. Biol.*, 96:529–534 (1983).

Louzada, Jr. et al., "Glutamate release in experimental ischaemia of the retina: an approach using microdialysis" *J. Neurochem.*, 59:358–363 (1992).

MacManus et al., "Global ischemia can cause DNA fragmentation indicative of apoptosis in rat brain" *Neurosci. Lett.*, 164:89–92 (1993).

Maragos et al., "Glutamate dysfunction in Alzheimer's disease: an hypothesis" *Trends Neurosci.*, 10:65–68 (1987).

Massey, in *Progress in Retinal Research*, eds. Osborne N. N. and Chader, G. J., Permagon Press, Oxford 9, 399–426 (1990).

Mattson, "Excitory amino acids, growth factors and calcium: a teeter-totter model for neural plasticity and degeneration" *Adv. Exp. Med. Biol.*, 268:211–220 (1990a).

Mattson, "Antigenic changes similar to those seen in neurofibrilary tangles are elicited by glutamate and Ca2+ influx in cultured hippocampal neurons" *Neuron*, 4:105–117 (1990b).

Meister, "Modulation of intracellular levels of glutathione" in *Biochemical Modulation of Anticancer Agents: Experimental and Clinical Approaches* (eds. Valeriote, F. A., and Baker, L. H.) Martinus Nijhoff Publishing, Boston/Dordrecht/Lancaster, 245–259 (1986).

Michaels and Rothman, "Glutamate neurotoxicity in vitro: antagonist pharmacology and intracellular calcium concentrations" *J. Neurosci.*, 10:283–292 (1990).

Moscona, "On glutamine synthetase, carbonic anhydrase and Muller glia in the retina" in Progress in Retinal Research (eds. Osborne N. N. and Chader G. J.) Permagon Press, Oxford, 2:111–135.

Moscona et al., "Enzymatic induction in embryonic retina: the role of transcription and translation" *PNAS (USA)*, 61:160–167 (1968).

Mosinger et al., "Blockade of both NMDA and non-NMDA receptors is required for optimal protection against ischmeic neuronal degeneration in the in vivo adult mammalian retina" *Exp. Neurol.*, 113:10–17 (1991).

Moudy et al., "Rapid desensitization determines the pharmacology of glutamate neurotoxicity" *Neuropharmacology*, 33:953–962 (1994).

Nadler et al., "Intraventricular kainic acid preferentially destroys hippocampal pyramidal cells" *Nature*, 271:676–677 (1978).

Neal et al., "Effects of ischaemia on neurotransmitter release from the isolated retina" *J. Neurochem.*, 62:1025–1033 (1994).

Neuwelt et al., "Is there a therapeutic role for blood-brian barrier disruption?" *Ann. Int. Med.*, 93:137–139 (1980).

Norenberg, "Immunohistochemical study of glutamine synthetase in brain trauma" J. Neuropathol. Exp. Neurol., 4:347 (1982).

Olney et al., "The role of specific ions in glutamate neurotoxicity" *Neurosci. Lett.*, 65:65–71 (1986).

Olney et al., "NMDA antagonist neurotoxicity: mechanism and prevention" *Science*, 254:1515–1518 (1991).

Olney, "Glutamate, a neurotoxic transmitter" *J. Child Neurol.*, 4:218–226 (1989).

Olney, "New mechanisms of excitatory transmitter neurotoxicity" *J. Neural Transm. Suppl.*, 43:47–51 (1994a).

Olney, "Neurotoxicity of NMDA receptor antagonists: An overview" *Psychopharmacol. Bull.*, 30:533–540 (1994b)

Olney et al., "NMDA antagonist neurotoxicity: mechanism and prevention" *Science*, 254:1515–1518 (1991).

Pardridge, et al., 1992, "Blood-brain barrier and new approaches to brain drug delivery" *West J. Med.* 156(3) 281–286

Pardridge, 1992, "Recent Developments in peptide drug delivery to the brain" *Pharm. Toxicol.* 71(1):3–10

Patejunas and Young, "Developmentally regulated primary glucocorticoid hormone induction of chick retinal glutamine synthetase mRNA" *J. Cell Biochem.*, 35:205–216 (1987).

Petito et al., "Brain glutamine synthetase increases following cerebral ischemia in the rat" Brain Res., 569:275–280 (1992).

Reisfeld and Vardimon, "Cell to cell contacts control the transcription activity of the glucocorticoid receptor" *Mol. Endocrinol.* 8:1224–1233 (1994).

Ronzio et al., "Studies on the mechanism of inhibition of glutamine synthetase by methionine sulfoximine" *Biochemistry*, 8:1066–1075 (1969).

Rosner et al., "Methylprednisoline ameliorates retinal photic injury in rats" Arch. Ophthalmol. 110:857–861 (1992a)

Rosner et al., "Therapeutic parameters of methylprednisolone treatment for retinal photic injury in a rat model" *Res. Commun. Chem. Pathol. Pharmacol.*, 77:299–311 (1992b)

Rothman and Olney, "Glutamate and the pathophysiology of hypoxic-ischemic brain damage" *Ann. Neurol.*, 19:105–111 (1986).

Rothman, "Synaptic release of excitatory amino acid neurotransmitters mediate anoxic neuronal death" *J. Neurosci.*, 4:1884–1891 (1984).

Rowe et al., "Glutamine synthetase (sheep brain)" in *Methods in Enzymology* (eds. Tabor, H. and Tabor, C. W.) Academic Press, New York, 17A:900–910 (1970).

Sandberg et al., "Effect of corticostriate pathway lesion on the activities of enzymes involved in synthesis and metabolism of amino acid neurotransmitters in the striatum" *J. Neurochem.*, 44:42–47 (1985).

Simon et al., "Blockade of N-methyl-D-aspartate receptors may protect against ischemic damage in the brain" *Science*, 226:850–852 (1984).

Spencer et al., "Lathyrism: evidence for role of the neuroexcitory amino acid BOAA" *Lancet*, 239:1066–1067 (1986)

Tanaka et al., "Reaction of astrocytes in the gerbil hippocampus following transient ischemia: immunohistochemical observations with antibodies against glial fibrillary acidic protein, glutamine synthetase, and S-100 protein" *Exp. Neurol.*, 116:264–274 (1992).

Tecoma et al., "Traumatic neuronal injury in vitro is attenuated by NMDA antagonists" Neuron, 2:1541–1545 (1989).

Van der Berg and Garfinkel, "A simulation study of brain compartments-metabolism of glutamate and related substances in mouse brain" Biochem. J. 123:211–218 (1971).

Van der Hoff et at., "cDNA sequence of the long mRNA for human glutamine synthetase" *Biochem. Biophy. Res. Commun.*, 190:249–251 (1991).

Vardimon et al., "Developmental regulation of glutamine synthetase and carbonic anhydrase II in neural retina" *Proc. Natl. Acad. Sci., USA*, 83:9060–9064 (1986).

Vardimon et al., "Cell contacts are required for induction by cortisol of glutamine synthetase gene transcription in the retina" *Proc. Natl. Acad. Sci., USA*, 85:5981–5985 (1988).

Waniewski and Martin, "Exogenous glutamate is metabolized to glutamine and exported by rat primary astrocyte cultures" *J. Neurochem.*, 47:304–313 (1986).

Waniewski and Martin, "Characterization of L-glutamic acid transport by glioma cells in culture: Evidence for sodium-independent, chloride-dependent high affinity influx" *J. Neurosci.*, 4:2237–2246 (1984).

Wilkins and Rengachary, *Neurosurgery, Volume II, chapter* 190 (McGraw Hill).

Zeevalk et al., "Excitatory amino acid-induced toxicity in chick retina: amino acid release, histology, and effects of chloride channel blockers" *J. Neurochem.*, 53:1610–1619 (1989).

Zeevalk and Nicklas, "Chemically induced hypoglycemia and anoxia: relationship to glutamate receptor-mediated toxicity in retina" *J. Pharmacol. Exp. Ther.*, 253:1285–1292 (1990).

Zhang and Young, "A single upstream glucocorticoid response element juxtaposed to an AP1/ATF/CRE-like site renders the chicken glutamine synthetase gene hormonally inducible in transfected retina" *J. Biol. Chem.*, 266:24332–24338 (1991).

What is claimed is:

1. A method for slowing ischemic induced damage which result in secondary neuronal degeneration by administering to a patient an effective dose of glutamine synthetase, wherein said effective dose slows the delayed secondary neuronal degeneration of NMDA-glutamate receptor-containing cells when compared to degeneration in an untreated patient.

2. The method of claim 1 wherein the patient is a human.

3. The method of claim 1 wherein the patient is a non-human mammal.

4. The method of claim 1 wherein the neuronal degeneration is in the peripheral nervous system.

5. The method of claim 1 wherein the neuronal degeneration is in the central nervous system.

6. The method of claim 1 wherein glucocorticoid steroids are co-administered to the patient.

7. A method for slowing ischemic induced damage as set forth in claim 1 wherein the ischemic induced damage is retinal damage.

* * * * *